United States Patent [19]

Schulze

[11] Patent Number: 5,413,584
[45] Date of Patent: May 9, 1995

[54] "OMEGA"-SHAPED STAPLE FOR SURGICAL, ESPECIALLY ENDOSCOPIC, PURPOSES

[75] Inventor: Dale Schulze, Hamburg, Germany

[73] Assignee: Ethicon, Inc., Somerville, N.J.

[21] Appl. No.: 59,147

[22] Filed: May 7, 1993

[30] Foreign Application Priority Data

May 11, 1992 [DE] Germany .................. 42 15 449.9

[51] Int. Cl.⁶ ............................................ A61B 17/04
[52] U.S. Cl. .................................. 606/219; 606/143; 227/19; 411/457
[58] Field of Search ............... 606/219, 143, 148, 151; 227/19; 411/457, 920

[56] References Cited

U.S. PATENT DOCUMENTS

| | | | |
|---|---|---|---|
| 2,236,581 | 4/1941 | Schenck | 411/457 |
| 3,958,576 | 5/1976 | Komiya | 128/346 |
| 4,014,492 | 3/1977 | Rothfuss | 227/19 |
| 4,261,244 | 4/1981 | Becht et al. | 411/472 |
| 5,156,609 | 10/1992 | Nakao et al. | 606/143 |
| 5,242,457 | 9/1993 | Akopov et al. | 606/148 |

FOREIGN PATENT DOCUMENTS

| | | | |
|---|---|---|---|
| 0085930 | 8/1983 | European Pat. Off. | A61B 17/08 |
| 0337874 | 10/1989 | European Pat. Off. | A61B 17/10 |
| 3204532 | 12/1983 | Germany | A61B 17/08 |
| 3238892 | 4/1984 | Germany | 606/151 |
| 1364322 | 1/1988 | U.S.S.R. | 606/151 |
| 89/04146 | 5/1989 | WIPO | A61B 17/08 |

Primary Examiner—Gary Jackson
Attorney, Agent, or Firm—Paul A. Coletti

[57] ABSTRACT

The invention relates to a staple for surgical purposes, made from bendable wire-like material. According to the invention, a staple is so designed that the base is shaped bent backwards from its tissue fastening surface, starting from its center section, on both sides, opposite to the direction of the legs, so far that the ends of the base touch or come close to each other, the base and legs thereby forming an essentially Ω-shaped contour. The bent-back configuration effects a substantial reduction in the width of the staple when it is pushed forward through the trocar cannula, so that endoscopically larger staples than usual can be set with a suitable fastening mechanism.

14 Claims, 4 Drawing Sheets

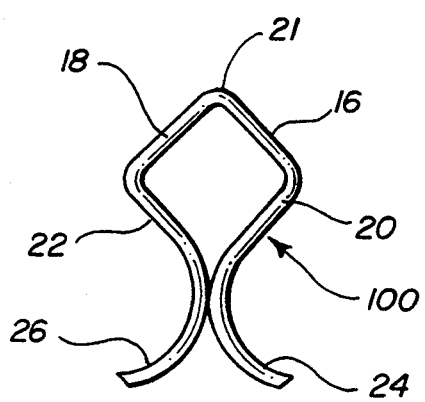
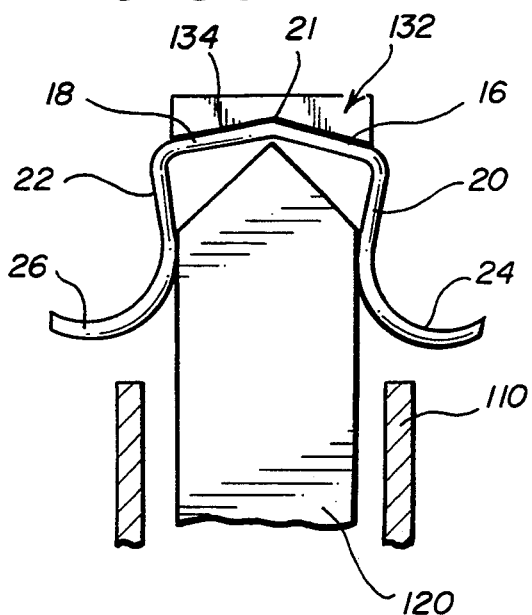
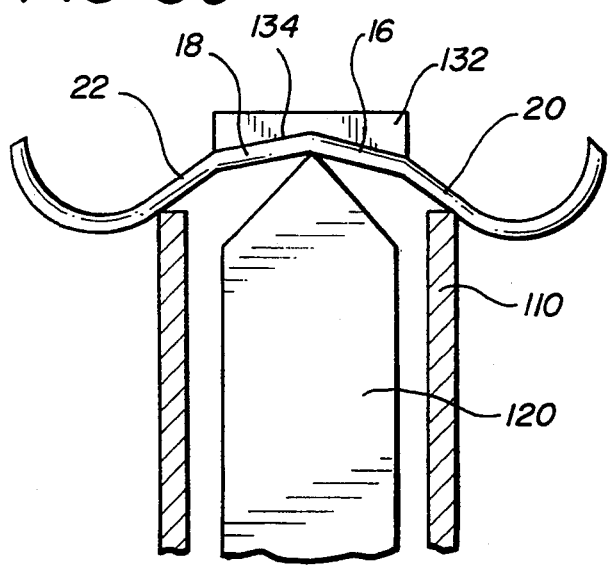
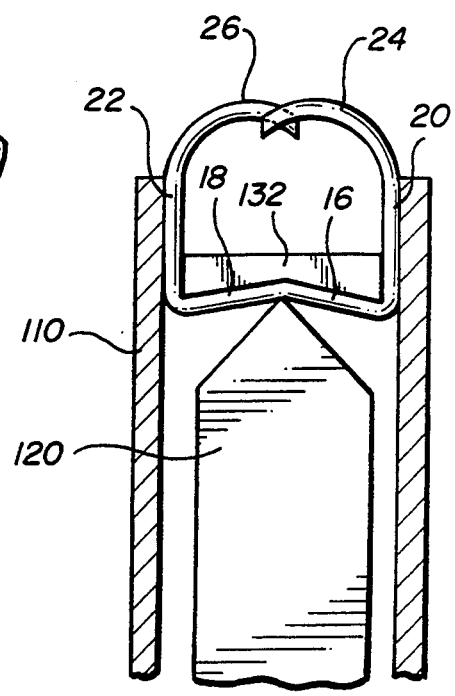

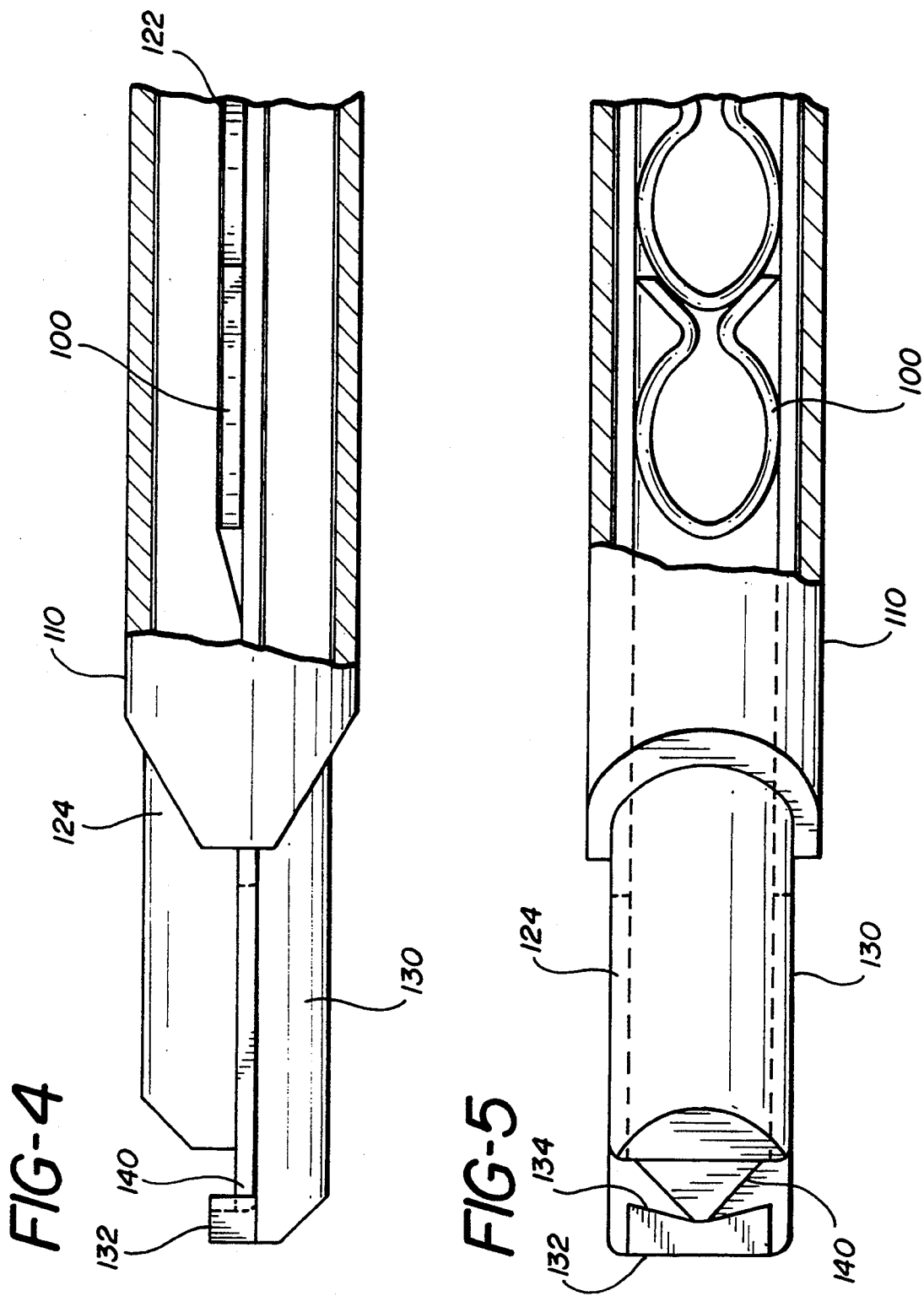

"OMEGA"-SHAPED STAPLE FOR SURGICAL, ESPECIALLY ENDOSCOPIC, PURPOSES

FIELD OF THE INVENTION

This invention relates to a staple for surgical purposes, especially for the bringing together of bundles of vessels and tissue structures under endoscopic operation conditions. The staple is made from bendable wire-like material and contains a base and limbs (or legs) projecting from each end thereof, the base being bent backwards opposite to the direction of the limbs, compared to their position at closure.

BACKGROUND OF THE INVENTION

Mechanical wound closures by means of staples or clips are used in practically all surgical areas, in order to bind tissue and hold it together. For example, clips are used during anastomoses in the whole digestive tract, from the esophagus to the rectum, and also generally when setting sutures. The clips applied in such cases are made from bendable wire-like material and are bent into a closed form, which firmly encloses the tissue lying in between. Such clips and staple applying mechanisms are shown in the complete Ethicon, Inc., Somerville, N.J. catalogue published in 1989, pages 119 to 127.

The clips are placed in the staplers in a form which largely corresponds to that known from office staples. The lower part of FIG. 6 shows correspondingly formed conventional staples, which has a rectilinear bottom side or base 10; from the two ends 12 and 14 of which extend legs or limbs 42 and 44, projecting essentially at right angles. In use, the clip is bent into the closed staple shown in FIG. 6a with the use of a clip applier, and wraps round the tissue lying in between. The closed staple is essentially rectangular in shape, the limbs 42, 44 essentially forming the upper side of the rectangle and the base 10 becoming the bottom and the two sides of the rectangle.

Surgical staples are also used in modern minimally invasive operation techniques. In these operations, mostly called endoscopic or laparoscopic, the instruments needed for operative measures are introduced into the body through one or more trocar cannulae to the operation area, for example into the abdominal cavity, and controlled there under endoscopic monitoring. The trocar cannulae have a small diameter, in order that only minimal wounds occur when the trocar cannula is introduced through the abdominal wall; two sizes often used by surgeons allow passage of 5 mm and 10 mm instruments.

Staplers which are to be used endoscopically must likewise be introduced into the operation area through such trocar cannulae, the clips contained in the stapler lying with their bottom sides perpendicular to the longitudinal axis of the trocar cannula, and pushed forward in this position within the stapler. This produces the condition that the length of the base of the clip must always be less than the internal diameter of the trocar cannula. Since, for medical reasons, trocar diameters are usually pre-set for 5 mm and 10 mm trocars, the problem to date has been that only clips with a relatively small base length (and thus with a small perimeter and small overall size) can be used in endoscopic operations through trocar cannulae. An example of such appliers are those found in U.S. Pat. No. 5,174,487 and Ser. No. 07/759,014 (docket No. SEN-83), now U.S. Pat. No. 5,246,156, herein incorporated by reference.

FIG. 6 shows a conventional clip prior to setting. It has a straight bottom side or base 10 from whose ends 12 and 14 legs 42 and 44 project respectively. It is easy to see that much of the perimeter of the finally formed, essentially rectangular clip in the upper part of FIG. 6 comes from the originally straight base 10. The height (h) and width (b) of the closed rectangular clip (as in FIG. 6a) are approximately linked to the length of the base 10 prior to setting ($L_{base}$) through the relationship $b+2h=L_{base}$, if one assumes that the base side (b) and the two lateral sides (1) of the set clip are formed from the base 10. A clip which has, for example, a width $b=8$ mm and a height $h=6$ mm after setting would, if formed conventionally, have a base length of some 20 mm. The clip to be introduced with its base transversely through a trocar cannula would thus require a trocar cannula with an internal diameter of more than 20 mm. Trocars of this size are not generally desirable as, when they are applied, the advantages of minimally invasive surgery would be somewhat compromised.

From German Patent No. 32 04 532 a surgical clip made from bendable wire-like material is known, in which before setting, the base does not run along a straight line but is bent backwards, opposite to the fully closed direction of the legs. In this way, the free ends of the legs and the vertex of the base lie approximately along one line. Because of this shape before setting, the staple is somewhat more compact than the clips described above, which have a straight base. The extension of the staple in DE 32 04 532 measured transversely with respect to the legs is, however, again significantly greater than the extension measured in the direction of the legs, so that introducing such staple also would require a large trocar cannula.

SUMMARY OF THE INVENTION

It is thus an object of the invention to provide a surgical staple which is introducible with a stapler through a trocar cannula having a pre-set diameter and which surgical clip is bendable into a closed form having a larger perimeter than conventional clips.

This object is achieved thanks to the staple with the features described and claimed herein. Advantageous versions are further defined in the various dependent claims.

The shaping of the clip according to the invention allows a staple with a much greater base length than is the case with the conventional configuration to be pushed forward through a trocar cannula with a given internal diameter. Staples with a greater periphery, i.e., thicker staples can thereby be used with the available trocar cannulae in endoscopic operations. The staple shaped according to the invention so that the conventionally rectilinear bottom side or base is formed back on itself before closure, so that its ends touch or at least come close to each other. The legs project, preferably bent slightly backwards, from the brought-together ends. In this way, the base and the legs essentially form the shape of the Greek letter omega ($\Omega$). The bent-back design of the base essentially reduces the effective transverse lateral extension, critical for transport through the trocar cannula, so that larger clips are introducible into the operation area for a given trocar diameter.

DESCRIPTION OF THE DRAWINGS

The invention is described below with reference to the drawings, which show:

FIGS. 3a, 3b, 3c and 3d are plan views of chronologically successive forms during setting of the staple;

FIG. 4 is a side view of the distal end of a stapler for applying this staple in partial cross section;

FIG. 5 is a plan view of the stapler from FIG. 4 in partial section; and

DESCRIPTION OF THE INVENTION

Figure 1:
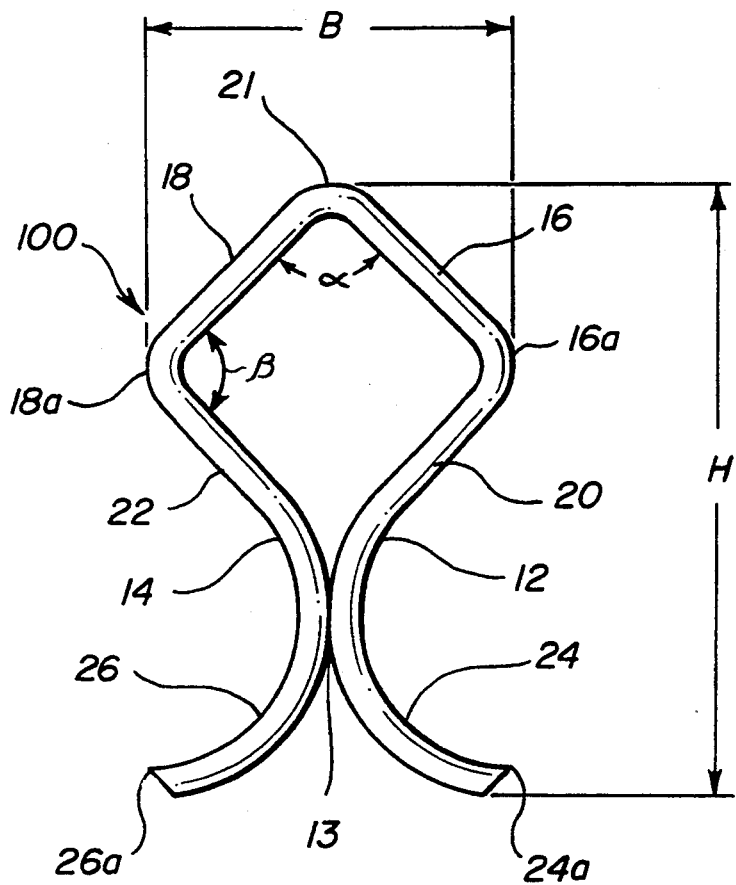
FIG. 1 is a first embodiment in plan view of a staple formed according to the invention.
Figure 2:
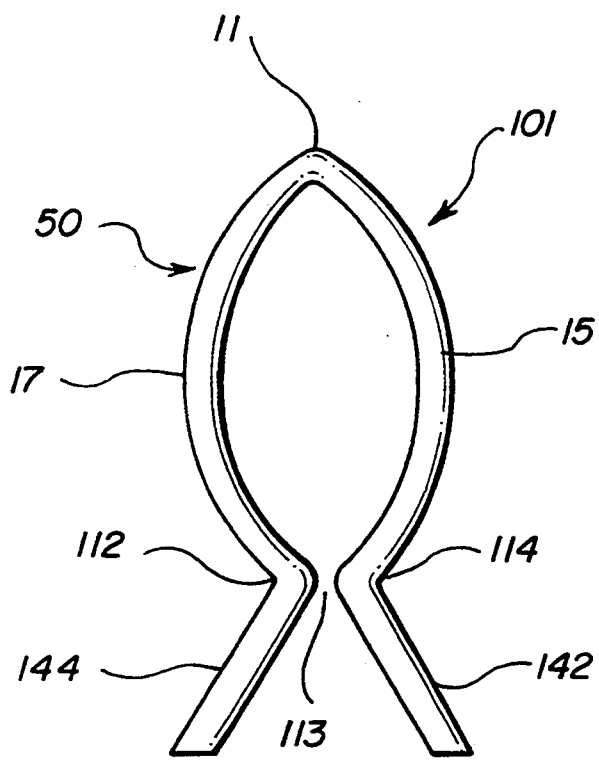
FIG. 2 is another embodiment of the staple in plan view.

FIGS. 1 and 2 show embodiments of the staple according to this invention which are introducible through a trocar cannula. The staple 100 shown in FIG. 1 obtains its bent-back form through first essentially rectilinear sections 16 and 18 which extend to both sides from a central bend or kink 21 at the top, and second essentially rectilinear sections 20 and 22 attaching respectively thereto. The first and second essentially rectilinear sections 16, 18, 20, 22 together form an essentially closed, rhombus-like contour. In the embodiment represented, the first rectilinear sections 16 and 18 form an angle $\alpha$, and the first and second rectilinear sections 18 and 22 as well as 16 and 20, respectively, form an angle $\beta$, both roughly corresponding to a right angle. The second essentially rectilinear sections 20 and 22 change continuously at their lower end into a curve to which the outwardly curved limbs 24 and 26, respectively, are continuously attached.

Figure 6A:
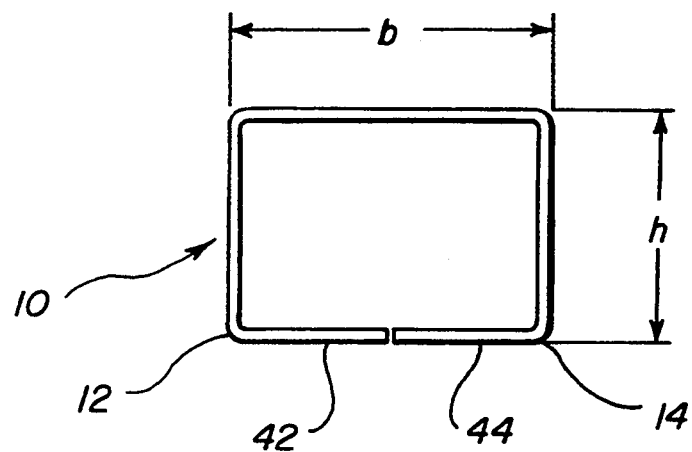
FIG. 6a is a plan view of a closed prior art staple.
Figure 6:
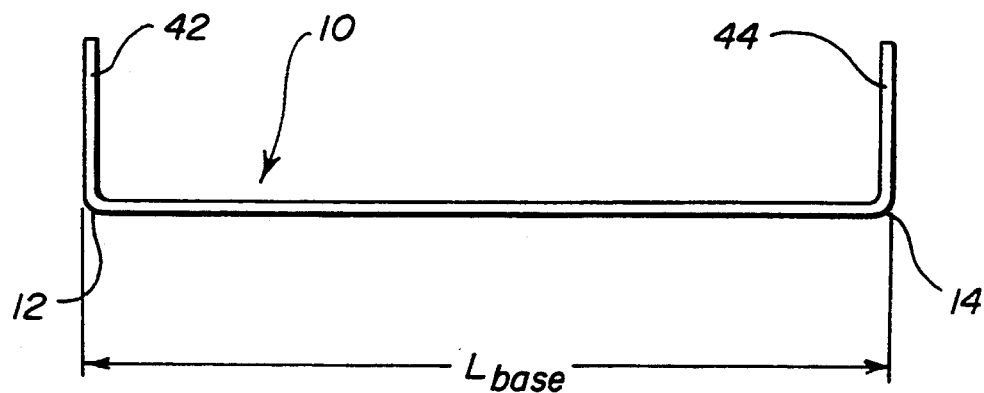
FIG. 6 is a plan view of an open prior art staple.

The staple 100 represented is symmetrical in relation to a straight line which runs through the tip 21 of the clip and through the point of contact 15 of the limbs 24 and 26. The width which is essential for the passage through the trocar cannula, i.e., the lateral extension in relation to the symmetrical straight line, is much reduced by the shaping of staple 100 according to the invention, when compared with conventional staples. A staple 100 which is 8 mm wide and 6 mm high after setting has a width B=6 mm and a height H=10 mm with the shaping according to the invention, which is to be compared with the base length, i.e. the effective width, of 20 mm in the above example for a conventional staple 10 of FIG. 6. This considerable reduction in width allows the use of larger staples in the current trocar cannulae.

It can also be seen that the reduction in the lateral extension is achieved at the cost of a greater extension in the length or height. The staple 100 is advantageously formed in such a way that the maximum lateral extension (B) is the same, namely the width in the transitional region between the first and second rectilinear sections (16a of sections 16, 20 and 18a of sections 18, 22) and at the outside tips 24a, 26a of the limbs 24, 26.

FIG. 2 shows a second embodiment of a staple 50 according to the invention. At its tip, the staple 50 has a bend or kink 11 in the center of the base, which corresponds to the kink 21 from the embodiment in FIG. 1. In principle, the base 101 can also be shaped throughout with continuous curvature, but the configuration with a kink 11 or 21 at the tip is advantageous, as is explained further below. In the embodiment represented, continuously curved section 15 and 17 extend to both sides from the kink 11, which sections, after exceeding a maximum lateral extension, run together again at point 113 and touch or come close to each other with their respective end sections 112, 114. In this embodiment, rectilinear limbs 142 and 144 extend from these.

FIGS. 3a to 3d display chronologically successive stages in the setting of the staple 100, in order to illustrate how it functions. FIG. 3a shows as starting point a staple 100 which largely agrees with the embodiment from FIG. 1. The staple 100 is pushed forward through the trocar cannula in a stapler, as described below, the staples 100 lying arranged one behind the other in a magazine or cartridge as in a conventional stapler such as those incorporated by reference above. The staples 100 are positioned in a manner so that the tip 21 of one respective staple lies between the legs 24, 26 of the next clip. FIG. 3b shows the next stage in the shaping of the staple after it is pushed to the distal tip or anvil 132 of the stapler, which is indicated diagrammatically and described in more detail below. The staple 100 is pushed forward to the distal tip and held there by a clamping apparatus comprising an anvil 132 and a movable clamping Jaw 120. It will be seen that the first rectilinear sections 16 and 18 lie against the angled front face 134 of the anvil 132. The second rectilinear sections 20 and 22 are already spread apart by a clamping jaw 120 which was inserted from behind between the limbs 24 and 26 and clamps the tip 21 firmly against the anvil 132.

In the next step in FIG. 3c, a sliding sleeve 110 engages from behind at the outward-standing sections 22, 26 and 20, 24 and is pushed further forward against the held staples 100, as a result of which the staple is bent forward around the anvil 132. In this embodiment the first rectilinear sections 16, 18 lie against the anvil 132 and form the bottom side for the clip to be shaped. The second rectilinear sections 20 and 22 are bent forward by sliding sleeve 110 until they adopt the position shown in FIG. 3d. The second rectilinear sections 20, 22 project as sides essentially perpendicularly from the bottom side 16, 18 formed with a slight kink in the center. At the top side, the staple is closed by the slightly curved limbs 24 and 26. Overall, a shape results which is reminiscent of the capital letter B, a configuration which has proved advantageous in practice. After the staple 100 has been set in the shape shown in FIG. 3d, the tissue lying in between is held safely together.

It can be seen that the configuration of the clip with a kink 11 or 21 in the embodiments of FIGS. 1 and 2 has, inter alia, the advantage that the clip is more easily positionable in the correct position in front of an anvil 132 with a complementarily angled surface, the kink being pushed into the recess of the angled front surface 134 of the anvil 132.

The clip preferably consists of a wire with a rectangular cross section of 0.5 mm×1 mm, made from a titanium alloy. Proposed as preferred dimensions for the staple in FIG. 3a are a width of B=6 mm and a height of H=10 mm, which gives a set staple in FIG. 3d with a width of roughly b=8 mm and a height of roughly h=6 mm.

FIGS. 4 and 5 show a stapler in which the distal end is introduced through a trocar cannula as represented in side view in FIG. 4 and in plan view in FIG. 5. The device has an elongated support rod 130 which carries at its distal end a projecting anvil 132 which is designed with a slightly angled front face 134. Seated on the guide rod 130 is a magazine 122 in which a supply of staples 100 is held ready. The staples 100 are arranged lying one behind the other in a row in the magazine 122, so that the tip of each omega-shaped staple 100 lies between the limbs of the staple in front of it. The row of staples is advantageously biased by a pre-stressing force, for example by a spring which presses the staples against each other and forward, so that the respective frontmost clip is brought into the area of the clip-shaping or clip-setting mechanism of the apparatus. Also provided is a clamping jaw 140 which is designed with a front tip in order to engage in the recess of the angled surface 134 of the anvil 132. Clamping jaw 140 is displaceable in longitudinal direction on the guide rod 130 and guided under the 100 in the magazine section 124, so that when clamping jaw 140 is drawn back the frontmost staple drops into the corresponding space between anvil 132 and clamping jaw 140. Guide rod 130, magazine 120 and clamping jaw 140 are enclosed by a sliding sleeve 110 which is displaceably guided in longitudinal direction.

For actuation, the stapler has at its proximal end (not shown) a conventional actuation mechanism which can comprise, for example, two oppositely swivellable grips or handles which lie in the user's hand. One of the grips is firmly connected to the guide rod 130 and the other swivellably attached thereat, the swivelling of the second grip transmitting movements onto the clamping jaw 140 and the sliding sleeve 110. To actuate the stapler, the second grip is swivelled, as a result of which the clamping jaw 140 is drawn off from the anvil 132 so that a free space forms between them. The frontmost staple 100, which is pushed forward by the following staples, slides into this free space, the frontmost staple 100 remaining on the support rod 130 with the tip before the anvil 132. The movement of clamping jaw 140 continues, so that after staple 100 has slid between anvil 132 and clamping jaw 140 the latter is pushed forward again, as a result of which it moves with its tip between the limbs of staple 100 and bends the latter upwards. Delayed against the backward and forward movement of clamping jaw 140, sliding sleeve 110 is pushed forward by the actuation mechanism in order to close the staple in the manner shown in FIG. 3d. Sliding sleeve 110 then returns to its rest position and anvil 132 is likewise drawn back in order to release the set clip.

The staples 100 are aligned in the magazine 122, each kept ready with the tip engaging in the end section of the clip in front of it, a typical magazine size having provision for ten clips. The magazines can easily be made from plastics as a cartridge and insertable into the stapler. In such a configuration, the stapler with the handles and stapling mechanism is a reusable instrument into which, for the use in question, a magazine 122 with the staples 100 according to the invention is inserted.

What is claimed is:

1. In combination:
    a staple for surgical purposes, made from bendable material, which has a base with a pair of ends and a pair of legs projecting from said base respective ends, said base having a tissue contacting surface and said base being shaped with a bend opposite to said tissue contacting surface and opposite an anvil for forming said staples so that the ends of said base are adjacent to one another, such that said base and legs form an essentially Ω-shaped contour; and
    a stapler for forming said staple comprising a housing, said stapler having at least an anvil and a staple former contained within said housing for forming said staple around said anvil, said staple held adjacent said anvil, and said anvil having a staple contacting surface, such that said tissue contacting surface of said anvil is engageable with said staple contacting surface during the forming of said staple.

2. Combination according to claim 1, characterized in that the shape formed by the base and legs is essentially symmetrical in relation to a straight line passing through the center of the base and said base ends.

3. Combination according to claim 1, characterized in that the legs are bent away from said base ends so far that the staple has the same width at said ends as the maximum width of said bent-back base.

4. Combination according to claim 1, characterized in that the base has a bend at in its center.

5. Combination according to claim 1, characterized in that the legs are shaped with a curvature which is opposite to the curvature of said base.

6. Combination according to claim 1, characterized in that the staple is made from a titanium alloy.

7. The combination of claim 1 wherein said anvil has an angled staple contacting surface which conforms to the tissue contacting side of said base.

8. Combination of claim 1 wherein said staple is made from stainless steel.

9. Staple for surgical purposes, made from bendable material, which has a base with a pair of ends and a pair of legs projecting from said base respective ends, said base having a tissue contacting surface and said base being shaped with a bend opposite to said tissue contacting surface so that the ends of said base are adjacent to one another, such that said base and legs form an essentially Ω-shaped contour characterized in that a pair of first straight sections extend from the bend in the center of said staple to each side of said bend, said sections forming an essentially right angle.

10. Staple for surgical purposes according to claim 9, characterized in that the said straight sections has extending from their opposite end a corner which turns into a second straight section, as a result of which the second straight sections run onto each other.

11. In combination:
    a staple for surgical purposes, made from bendable material, which as a base with a pair of ends and a pair of legs projecting from said base respective ends, said base having a tissue contacting surface and said base being shaped with a bend opposite to said tissue contacting surface and opposite an anvil for forming said staples so that the ends of said base are adjacent to one another, such that said base and legs form an essentially Ω-shaped contour; and
    a stapler for forming said staple having a housing:
        an anvil and a staple former contained within said housing for forming said staple around said anvils, said staple held adjacent said anvil, and said anvil having a staple contacting surface, such that said tissue contacting surface of said anvil is engageable with said staple contacting surface, and
        a driver for driving said staple against said anvil during the forming of said staple.

12. The combination of claim 11 wherein said anvil has an angled surface which conforms to the tissue contacting side of said base.

13. The combination of claim 11 wherein said driver is wedge shaped.

14. A method for fastening tissue in a body comprising:

inserting a trocar cannula into said body, said trocar having an external diameter; and applying a tissue fastener to said tissue, said tissue fastener inserted through said trocar cannula by a tissue fastening mechanism containing an anvil, wherein said tissue fastener has a pre-formed width less than the external diameter of said cannula; and wherein said tissue fastening mechanism contains a former which forms said tissue fastener about said anvil such that said tissue fastener has a formed width which is greater than the diameter of said external diameter of said cannula.

* * * * *